United States Patent [19]

Gibson

[11] 4,260,393

[45] Apr. 7, 1981

[54] METHOD AND COMBINED TEST ELEMENTS FOR DETECTION OF HEME

[75] Inventor: Jacob J. Gibson, Alexandria, Va.

[73] Assignee: Technology Resources, Inc., Washington, D.C.

[21] Appl. No.: 3,260

[22] Filed: Jan. 15, 1979

Related U.S. Application Data

[63] Continuation-in-part of Ser. No. 896,000, Jun. 3, 1977, which is a continuation-in-part of Ser. No. 803,106, Jun. 3, 1977, abandoned, and Ser. No. 696,459, Jun. 16, 1976, abandoned.

[51] Int. Cl.³ .................. G01N 33/52; G01N 33/72
[52] U.S. Cl. .................. 23/230 B; 23/913; 252/408; 422/56; 422/61; 435/4; 435/28; 435/805
[58] Field of Search .............. 23/230 B, 913; 422/56, 422/61; 435/4, 28

[56] References Cited

U.S. PATENT DOCUMENTS

| | | | |
|---|---|---|---|
| 2,838,377 | 6/1958 | Fonner | 23/230 B |
| 3,996,006 | 12/1976 | Pagano | 422/50 |
| 4,175,923 | 11/1979 | Friend | 422/56 |

*Primary Examiner*—Sidney Marantz
*Attorney, Agent, or Firm*—Howard L. Rose

[57] ABSTRACT

A diagnostic method and indicator for heme in controlled sensitivity is provided by impregnating a bibulous body, such as a test strip with a solution of a color indicator in leuco form and drying and storing in stable active form, and in use applying to the strip a test sample containing heme. The test color is then developed in the strip by wetting the test sample and strip in contact therewith with a peroxide solution of a solvent for the leuco dye carrying the oxygen released from the peroxide by the heme peroxidase in the test sample, such as blood or body tissue or residues containing occult blood whose presence is to be determined.

11 Claims, No Drawings

METHOD AND COMBINED TEST ELEMENTS FOR DETECTION OF HEME

This invention is a continuation-in-part of my co-pending application Ser. No. 896,001 filed June 3, 1977, in turn a continuation-in-part of Ser. No. 803,106 filed June 3, 1977, abandoned, and Ser. No. 696,459 filed June 16, 1976, abandoned, and relates to a combined test strip or dipstick and developing solution used therewith for indicating the presence of heme (haem) in a test sample applied to the strip by color developed in the strip, and more particularly to a method and combined strip and developer for indicating the presence of heme in a test sample applied to a desensitized test strip to positively indicate the presence of heme in a significant substantially desensitized test, and the test method.

The test strip hereof comprises a bibulous carrier to which is applied a solvent soluble leuco dye and the developer hereof comprises a solvent, both for peroxide and the leuco dye, while also serving as a carrier for the active oxygen released from the peroxide by the heme peroxidase in the test sample to allow interaction to develop color by the released oxygen with the leuco dye. The leuco dyes hereof are sensitive to develop color in the dye only at higher heme peroxidase concentrations, such as concentrations in the range of about one part of heme peroxidase in thirty thousand parts down to five thousand parts or less of diluted test specimen, whereby the dye selected and developer are practically desensitized for more reliable determination of the presence of heme in a significant quantity in the test sample.

Heme is characterized by the substantial presence therein of ferrous peroxidase, a very active enzyme to release free active oxygen from peroxide. This enzyme is widely distributed in nature among many natural organic substances, such as plant and animal tissues other than blood per se.

In prior art efforts to determine the presence of heme in a test sample, typically in blood, as is the primary object hereof, emphasis was placed upon obtaining greater and greater test sensitivities, such as to determine the presence of the enzyme in one part per hundred thousand parts of test sample, or at even higher dilutions of the test sample, and for this purpose highly acidized peroxides were used as a developer composition, whereby that widely distributed enzyme ferrous peroxidase, both in blood as well as in other organic cellular tissue throughout the plant and animal kingdom, tended always to react positively to indicate the presence of the enzyme in many organic materials other than blood, whereby the prior art tests were too sensitive to be practical for determination of heme in blood. Thus, it was known in the art to activate the peroxide with glacial acetic acid, generally active at one part of heme per 100,000 parts of test sample.

According to the present invention, the leuco dye in the solvent, preferably a lower mono hydric alkanol, having from about 1 to 6 carbon atoms, preferably 1 to 3 carbon atoms for rapid evaporation, is impregnated into a bibulous carrier such as a porous paper, the treated paper is then dried and usually cut into strips. The leuco dye may be a leuco white, or one which has a light color which will change distinctively to a recognizably distinct color in oxidized form.

It is preferred to use any of the polyamino diphenyls, typically o-tolidine, benzidine, o-dianisidine, m-tolidine, gum guaiac, mixtures of benzidine and guaiac, diaminofluorene and other derivatives of benzidine-like compounds, herein designated as diamino diphenyl compounds. The best of the diamino diphenyl dyes known at this time are o-tolidine, benzidine and gum guaiac. O-tolidine develops a blue color upon oxidation and can be quickly and completely oxidized at room temperature by the oxygen liberated from the peroxide developer solution by the action of the peroxidase of heme contained in the test sample.

The bibulous support is a porous paper, typically a laboratory filter paper such as standard Whatman II filter paper.

The leuco dye is dissolved in the alcohol and the bibulous carrier is dipped in the solution and dried, preferably in an inert gas stream. Any of the lower alkanols are a useful solvent herein, but it is preferred to use dry methanol, both because it dries more rapidly, will readily activate the leuco dye for reaction with a methanol solution of the developer, and when used in the developer it is more stable to activate the heme peroxidase, while inactivating possible conflicting catalases in the test material, such as myelo peroxidase, often present in many plant and animal tissue and which might interfere. The dye solution in alkanol is a dilute solution in concentration of about 0.5 to 3% of the leuco dye, such as the diamino diphenyl compound. Thus, the bibulous carrier is impregnated with the leuco dye in solution, dried and then stored preferably in an inert gas stream and stored in the dark and in air-free containers for stable storage.

The developing solution essentially is a dilute solution of peroxide, usually hydrogen peroxide or a peroxide compound which will be readily hydrolized to free oxygen by the heme ferrous peroxidase. The peroxide is dissolved in the solvent alkanol, both the leuco dye and the peroxide compound being soluble therein, usually the same solvent can be used in depositing the leuco dye on its bibulous support, as well as for the peroxide developer. It is preferred to use methanol for its several benefits, including particularly the fact that the methanol does not inactivate the ferrous peroxidase in the heme. The peroxide solution may contain a small catalytic quantity of stabilizer and a couple of drops of acetic acid.

The developing solution is formed by dissolving hydrogen peroxide such as a commercial 3% solution of hydrogen peroxide in water. The peroxy compound is dissolved in the solvent, usually in quantity of 20-80 parts of 3% hydrogen peroxide solution in water, the balance being alkanol solvent, usually methanol, preferably the developer is substantially 60-40 parts of methanol to 40-60 parts of 3% hydrogen peroxide solution in water, and the greatest shelf life stability is usually about in ratio of 1:1 methanol solvent to hydrogen peroxide solution in water. It is found that the peroxide solution thus formed can be further stabilized by additions of urea, in concentration ranging from 50-100 mg per liter to 50-100 mg per hundred cc's of solution. It is further found that a few, such as 1-2 drops of 10% acetic acid per hundred cc's of the developer solution tends to improve the color development by providing very slight acidity, less than will impart an excessive acidity test strip, such as a pH below about 4.5. Larger quantities of acetic acid tends undesirably to increase the sensitivity of the test.

The test hereof is intended to activate the test strip to convert the leuco dye to colored form by any substantial heme content in the test strip, but the preferred amino biphenyl dyes used are quite sensitive in a wide range, including great dilutions exceeding about 1 part in 5,000 up to 1 part in 30,000 in the test sample. It is preferred to reduce the sensitivity of the test to provide a reactivity of the heme in the test material, to activate the color in the dye upon the test strip when the concentration of the heme is present, ranging in quantity from at least about 1 part in 5,000 of the test material, down to about 1 part in 30,000, since this enzyme is wide spread in nature. Greater sensitivity than this tends to activate ferrous peroxidase even from other sources than blood and present in even much lesser quantities, such as 1 part in 50,000 or 100,000, but in such high sensitivities the certainty that the heme-containing material under test as originating from blood is less and it could well have originated from other organic sources. The reduction of the sensitivity to read upon the larger concentrations of heme increases the specificity and certainty that the color developed in the test strip is from the heme in the test material, and not other organic source of a reducing enzyme.

The test material as generally referred to above is any material containing blood heme, which is the object of testing herein. It can be a human tissue blood, usually blood itself taken from a living body or it may be occult blood in a body tissue or residue, such as feces, or blood which has been lost or deposited on any surface and whose nature is to be tested to determine whether the substance or scraping from any area, including any artifacts or place where blood may have been deposited, as a source of material from which it is to be determined that the nature of the substance is blood and the actual test is for the heme content therein.

THE TEST METHOD

The test method consists of first saturating a bibulous paper, or other carrier body with an alcoholic solution of a leuco dye as listed, preferably in methanol, the paper being dried, cut into strips and stored air-free, or an inert atmosphere and in the dark. The leuco dye selected, such as one of the diamino diphenyls will vary in sensitivity, so that the color sensitivity in large part can be varied both by selection of the dye material and using as developer a peroxide of higher pH such as above about 4.5.

| DYE | ONE PART BLOOD IN (PARTS) WATER |
|---|---|
| GUAIAC | (5,000) |
| O-TOLIDINE | (10,000) |
| BENZIDINE | (30,000) |

These sensitivities will be increased several fold by substituting other organic solvent carriers. For instance, the substitution of glacial acetic acid for a lower alkanol such as methanol will increase the sensitivity up to five times. As a practical matter, substantially any test material such as human feces will show a positive test and activate the test strip to develop the dye color using glacial acetic acid as the developer solvent, so that any heme that might be present and was desirably detected in the test sample, would be so sensitive to develop the dye color as in effect destroying the test. The developer is so sensitive that the presence of heme in concentration indicative of blood could not be determined when the developer solution contains substantial amounts of glacial acetic acid.

In performing the test, the test strip is covered by a smear of the test material and a drop of the developer solution is placed upon the smear and filtering through the test strip a blue color for the diamino dipheynal type of leuco dye will develop, showing the positive presence of heme in the test material. The heme from various sources, such as scrapings from a carpet, clothing or artifacts, sedimentary solid deposits from urine or feces as well as fresh or dried blood may be placed directly upon the test strip or the test material may be suspended in water and a drop or two then added to the test paper. Fluid suspensions of test material such as urine can be similarly poured upon the bibulous paper. The final step is the application of a drop of the developer upon the deposited test material upon the surface of the test paper, and the development of the blue color indicates a positive test for the presence of heme.

EXAMPLES

The following examples illustrate the practice of this invention:

EXAMPLE 1

(a) PREPARATION OF TEST PAPER

Two grams of gum guaiac dissolved in a 100 cc of absolute methanol, a sheet of No. 1 Whatman filter paper is dipped in the solution, the paper is then dried in a stream of nitrogen gas and may be cut into strips. It is then stored in a substantially air-free container and left in the dark.

(b) PREPARATION OF DEVELOPING SOLUTION 0.1 grams of urea is dissolved in a 100 cc of aqueous 3% hydrogen peroxide solution and both are then mixed with 100 cc of absolute methanol. 0.2 cc of 10% acetic acid is then added, that solution is then ready for use as the developing solution.

(c) TEST PROCEDURE

The combination described in (a) and (b) above is sensitive to indicate the presence of heme in human blood, in concentrations up to about 1 part of heme in 5,000 parts of test sample. A strip prepared as in (a) has applied a thin smear of human feces and the strip is then wet with one drop of the developer solution prepared as in (b). The test paper will develop a blue color if the heme is present in the test sample in at least that concentration, of 1 part in 5,000 of the test sample. At lower concentrations of heme in the test no color will be developed in the test paper.

EXAMPLE 2

The test in example 1 was repeated, but the test material was modified as a suspension of human blood in water, to a concentration of 1 part of heme in 7,500 parts of the solution by volume, and a drop of the test solution was placed upon the filter paper of example 1. It showed no color development. The test was then repeated with human blood diluted with water to a concentration having a heme content of 1 part in 4,000 cc of solution, and one drop of the test solution applied to the same test strip readily caused the filter paper strip of example 1 to develop a blue color, thus indicating the difference in sensitivity, that gum guaiac is sensitive to a color development up to 1 part in 5,000 namely at 1 part in 4,000, but not a higher dilution such as 1 part in 7,500, by volume.

EXAMPLE 3

A sheet of filter paper was dipped in a 2½ gram solution of o-tolidine in 100 cc of absolute methanol; the wetted paper is then dried in a stream of nitrogen; cut into strips; and is then packaged and stored air-free in the dark, ready for use as described in example 1. The test procedure here followed was the same as both tests applied in example 2. The strips thus prepared were wet with a drop of diluted blood suspended in water and having a heme content of approximately 1 part in 7,500 of test solution. The test solution was found to develop color in the strip using the same developer prepared as in example 1, indicating that the leuco o-tolidine test strip was sensitive to show the presnce of heme in the lower concentration, more sensitive than the gum guaiac tested in examples 1 and 2. It was also sensitive to show the presence of heme in 4,000 parts of the test material as in example 2, using the same developer solution. A third test composition was prepared by again suspending human blood in water to form a dilute test material having about 1 part of heme in 15,000 parts of test solution, and the strip was tested therewith using the same developer as formed in example 1. However, in this case the solution in example 2 was also too dilute, indicating that the o-tolidine strip also was not sensitive to detect heme in concentrations of such high dilution. In repeating the tests, it was found that the approximate sensitivity of the o-tolidine strip to detect heme is approximately 1 part of heme in 10,000 parts of the test material, by volume, using the developer.

EXAMPLE 4

A test strip was again formed using a 2 gram solution of benzidine in absolute methanol, the dipped porous paper sheet being dried and cut into strips and stored as described in example 1. This strip was then wet with each of the previous test solutions of human blood as described in examples 2 and 3, treated with the same developer and developed a color indicating the presence of heme, even having a sensitivity to the test solution having 1 part of heme in 15,000 parts of test solution. Further test solutions were made up of human blood in water in concentrations of 1 part in 25,000 and 1 part in 35,000 parts of the test material, and the benzidine strip developed color using the same developer solution of example 1 for the test solution of 1 part in 25,000 parts, but was not sensitive to detect heme in test solutions as dilute as 1 part in 35,000 parts. The application of additional tests in various dilutions of the test material indicated that the threshold sensitivity of this strip was about 1 part in 30,000 parts of test solution.

EXAMPLE 5

Other sources of heme, such as scrapings of dried blood from surfaces, including clothing or carpet, including organic materials or tissues that may have contained blood were tested by applying the dried material as a dusted layer of the test strip of example 1, and the presence of heme was detected by wetting with a drop, sometimes two, of the same developer solution upon the test strip carrying the benzidine, when the heme content was not substantially greater than 1 part in 30,000 parts in the test material.

EXAMPLE 6

The test using the test strip of example 2, was applied to two drops of urine, applied to the gum guaiac test strip for detection of heme therein, and the developer developed color to show its actual presence when it was present in the range of sensitivity of that strip up to 1 part in 5,000 parts.

EXAMPLE 7

In a further series of tests repeating the procedure of example 1(b), but substituting glacial acetic acid as the solvent in quantity of a 100 cc per 100 cc of the same 3% aqueous hydrogen peroxide solution, whereby the quantity of glacial acetic acid to peroxide is in ratio of 1:1 as developer solution, and using the o-tolidine test strip of example 3. The sensitivity of that test strip was found to be active when the heme content of the test sample was reduced to as low as one part in 100,000. Thus indicating that the sensitivity of this same test strip increased to one part in 100,000 of heme when the developer solution was highly activated by a large quantity of glacial acetic acid.

EXAMPLE 8

Again, the same test strip of example 3, similarly impregnated with o-tolidine was found to be sensitive to a heme content of less than 1 part in 30,000 when developed with a solution of a strontium peroxide in quantity of 2½ grams dissolved in 100 ccs of absolute methanol.

It is thus clear that the sensitivity of the test is controllable, both by the leuco dye and the developer solution. Thus gum guaiac generally sensitive to a heme content test of 1 part in 5,000 becomes increased somewhat to about 1 part in 10,000 when the acidity of the hydrogen peroxide developer is greatly increased by substituting glacial acetic acid for the solvent in quantity exceeding 10% of the hydrogen peroxide solution. The benzidine dye having a sensitivity to methanol-peroxide developer solution of 1 part in 10,000 will also be increased to 1 part in 100,000 by using a more sensitive developer of about equal quantities of aqueous 3% hydrogen peroxide solution and glacial acetic acid. The o-tolidine also will have its sensitivity increased to indicate the presence of heme in quantity of 1 part in 100,000 of the test sample when the developer solution too has equal parts of 3% aqueous hydrogen peroxide solution and glacial acetic acid.

Thus, the sensitivity of the leuco dye is controllable and it is preferred herein to use a combination of a leuco dye and developer solution controlled to a sensitivity greater than about 1 part of heme in 30,000 parts of test sample down to about 1 part in 5,000 of test sample, whereby the presence of heme in human blood is reliably indicated in the test sample.

As thus described, a test for heme is provided with a control sensitivity in a practical range of about one part of heme distributed in 5,000 parts of carrier material, down to 1 part of heme distributed in 30,000 parts of test or carrier material. The bibulous test material may be of any structure, serviceable to carry any dry dye in leuco form, preferably stored unexposed to light or atmosphere before use, whereby it will remain stable in storage until used as a test strip. The coating thereon, the leuco dye will still allow the dye to be readily exposed and redissolved upon wetting with the alcoholic developer solution and which carries oxygen, formed proportionately in contact with the heme in the test material. That quantity of oxygen suffices to develop the color of the dye by oxidation, while being simultaneously dissolved and softened by the solvent of the developer solution.

In operation the sample of heme carrying material placed upon the bibulous paper is wet by the developer, the solution passes through and solubilizes the leuco dye therein, the developer solution comprising peroxide is converted to oxygen in contact with the ferrous peroxidase in the heme of the test sample. If any is present, the peroxide of the developer will be reduced proportionately to the quantity of heme that is present, forming free oxygen which becomes the essential oxidizing component of the developer oxidizing solution. This free oxygen when present in the developer solution reacts with the leuco dye solubilized by the solvent alkanol and thus develops the color by oxidation of the dye.

The bibulous paper may take the form of a dipstick in which a stiffened body, such as a wooden stick or a plastic base, may have an outer porous sheet fastened or wrapped thereabout as a laminate, at least the exposed layer thereof being coated with the leuco dye. In that structure it is sometimes useful to use even another, second outer layer to act as a filtering layer upon which the test material will be deposited and retained, so that the developer solution passing through to the leuco dye coating the inner layer will be free of other color contamination by the test material, and the leuco dye which the inner layer carries is reactive with the oxygen component and will be a clear color significant of the oxygen content of the developer solution alone.

Moreover, the bibulous layer may contain alkanol permeable plastics or thickeners, such as gelatin, polyvinyl alcohol readily penetrated by the alkanol solution, such polymeric substances serving only to protect the leuco dye to be readily penetrated by the developer solution.

Various modifications will occur to those skilled in the art, and accordingly it is intended that the description given above will be regarded as exemplary and not limiting, except as provided in the claims:

I claim:

1. The method of diagnostically testing the presence of heme in organic carrier material, comprising impregnating a bibulous test strip with a leuco dye, applying a test material for heme upon the bibulous test surface and wetting the test material with a developer solution, said developer solution comprising a peroxide solution in a solvent comprising methanol, said solvent also being a solvent for said leuco dye, whereby the developer solution passes in contact for hydrolysis of the peroxide by said heme, and then into contact with said leuco dye for oxidation thereof when heme is present, said dye and developer solution being sensitive to develop color in said leuco dye only when heme is present in the test material in quantity exceeding about 1 part of heme in 30,000 parts of test material.

2. The method of claim 1, wherein said leuco dye and developer solution are color sensitized to the range of 1 part of heme to 5,000 to 30,000 parts of test material.

3. The method as defined in claim 1, wherein the leuco dye is a diamino diphenyl compound.

4. The method as defined in claim 1, wherein the leuco dye is selected from the group consisting of gum guaiac, o-tolidine and benzidine.

5. The method as defined in claim 1, wherein the developer solution is a solution of about 3% hydrogen peroxide in quantity of 20-80%, the balance of said solution being substantially methanol, by volume.

6. The method as defined in claim 5, wherein said developer solution further contains a trace quantity of acetic acid.

7. The method as defined in claim 5, wherein said developer contains approximately 50-100 mg of urea per 100 cc of hydrogen peroxide.

8. A test combination for determining the presence of heme in a test sample, comprising the combination of a bibulous carrier body impregnated with a leuco dye, upon which a test substance containing heme may be applied, and a developer solution comprising a mixture of a soluble peroxide in quantity of 20-80%, the balance being substantially methanol for application to said test material supported in contact with said leuco dye impregnated bibulous carrier.

9. The combination defined in claim 8, wherein the leuco dye is a diamino diphenyl compound, said dye and developer solution imparting a sensitivity to heme in the test material in ratio of at least 1 part of heme to 30,000 parts of the test material.

10. The combination as defined in claim 8, wherein the leuco dye is a member of the group consisting of guaiac, o-tolidine and benzidine.

11. The combination as defined in claim 8, wherein said developer solution comprises about 20-80% of a 3% aqueous solution of hydrogen peroxide in methanol.

* * * * *